United States Patent [19]

Innes et al.

[11] 4,222,899

[45] Sep. 16, 1980

[54] AMMOXIDATION CATALYST

[75] Inventors: Robert A. Innes, Monroeville; William L. Kehl, Pittsburgh, both of Pa.

[73] Assignee: Gulf Research & Development Company, Pittsburgh, Pa.

[21] Appl. No.: 972,933

[22] Filed: Dec. 26, 1978

[51] Int. Cl.³ .................... B01J 21/06; B01J 23/18; B01J 23/22; B01J 23/28
[52] U.S. Cl. .................................. 252/469; 260/465.3
[58] Field of Search .................... 252/469; 260/465.3; 423/593, 598

[56] References Cited

U.S. PATENT DOCUMENTS

| | | | |
|---|---|---|---|
| 3,892,794 | 7/1975 | Grasselli et al. | 260/465.3 |
| 3,960,925 | 6/1976 | Gasson et al. | 260/465.3 |
| 4,008,179 | 2/1977 | Gasson et al. | 252/469 |

FOREIGN PATENT DOCUMENTS 1176233 1/1970 United Kingdom .................. 260/465.3

Primary Examiner—W. J. Shine

[57] ABSTRACT

Novel ammoxidation catalysts, particularly suitable in preparing acrylonitrile, containing critical amounts of (1) uranium, (2) antimony, (3) an element from Group IV B of the Periodic Table and (4) molybdenum and/or vanadium.

9 Claims, No Drawings

AMMOXIDATION CATALYST

BACKGROUND OF THE INVENTION

1. Field of the Invention

This invention is directed to novel ammoxidation catalysts, particularly suitable in preparing acrylonitrile, containing critical amounts of (1) uranium, (2) antimony, (3) an element from Group IV B of the Periodic Table and (4) molybdenum and/or vanadium.

2. Description of the Prior Art

In U.S. Pat. No. 4,040,983 to R. A. Innes and A. J. Perrotta, dated Aug. 9, 1977, there is disclosed and claimed a novel ammoxidation catalyst containing critical amounts of (1) uranium, (2) antimony and (3) an element from Group IV B of the Periodic Table. When such catalyst is used in the production of acrylonitrile from propylene, ammonia and molecular oxygen frequent regeneration of the catalyst is required in order to maintain its outstanding activity and selectivity for the production of acrylonitrile.

SUMMARY OF THE INVENTION

We have found that if we add a critical amount of molybdenum and/or vanadium to the Innes et al catalyst, the resulting catalyst can be used in the production of acrylonitrile from propylene, ammonia and molecular oxygen for a greatly increased period of time before requiring regeneration. Although the novel catalyst so produced is slightly less selective for the production of acrylonitrile, the combined yield of acrylonitrile and hydrogen cyanide, another desired chemical, is increased.

The novel catalyst claimed herein, particularly suitable for the production of acrylonitrile, is one wherein the atomic ratios of the components thereof are defined by the following empirical formula:

$$USb_aX_bY_cO_d,$$

wherein X is an element from Group IV B of the Periodic Table (titanium, zirconium or hafnium); Y is at least one element selected from the group consisting of molybdenum and vanadium; a is a number falling within the range of about 1.35 to about 2.75, preferably about 1.50 to about 2.50; and b is a number falling within the range of about 0.25 to about 1.65, preferably about 0.50 to about 1.50; c is a number falling within the range of about 0.05 to about 0.2, preferably aboout 0.08 to about 0.15; d is a number falling within the range of about 8 to about 12, preferably about 9 to about 11; and the sum of a+b is a number falling within the range of about 2.5 to about 3.5, preferably about 2.8 to about 3.3.

DESCRIPTION OF NOVEL CATALYST AND PROCESS FOR USING SAME

The novel catalysts claimed herein are prepared by heating at an elevated temperature an intimate mixture comprising (1) the oxides of uranium, antimony, an element from Group IV B of the Periodic Table, molybdenum and/or vanadium, or (2) compounds of these elements that are converted to said oxides upon heating. Examples of such oxides include $UO_2$, $U_3O_8$, $UO_3$, $Sb_2O_3$, $Sb_2O_4$, $Sb_2O_5$, $Ti_2O_3$, $TiO_2$, $ZrO_2$, $HfO_2$, $UTiO_5$, $USbO_5$, $USb_3O_{10}$, $MoO_3$, $MoO_2$, $V_2O_5$, $V_2O_4$, $V_2O_3$, etc. Examples of compounds that can be converted to such oxides upon preparation of the catalyst herein include $UO_2(NO_3)_2.6H_2O$, $UO_2C_2O_4.3H_2O$, $UO_2(C_2H_3O_2)_2.2H_2O$, $Sb_2(C_4H_4O_6)_3.6H_2O$, $Sb(C_2H_3O_2)_3$, $(NH_4(_2TiO(C_2O_4)_2.H_2O$, $Ti_2(C_2O_4)_3.10H_2O$, $Zr(C_2H_3O_2)_4$, $ZrO(C_2H_3O_2)_2$, $(NH_4)_6Mo_7O_{24}.4H_2O$, $VO(C_2O_4)_2$, or any hydrated oxide or hydroxide of antimony, uranium, titanium, zirconium, hafnium, molybdenum or vanadium.

In a preferred embodiment, intimate mixing is achieved by co-precipitation of the hydroxides or hydrated oxides from acidic solution by adding a suitable base, such as ammonium hydroxide. The acidic solution is conveniently prepared using various soluble salts as starting materials. These include $UO_2(NO_3)_2.6H_2O$, $UO_2(C_2H_3O_2)_2.2H_2O$, $UCl_3$, $UCl_4$, $UF_6$, $UBr_4$, $SbCl_3$, $Sb(C_2H_3O_2)_3$, $SbF_3$, $SbCl_5$, $Ti_2(C_2O_4)_3.10H_2O$, $TiOSO_4.H_2SO_4.8H_2O$, $ZrOCl_2.8H_2O$, $ZrO(C_2H_3O_2)_2$, and $ZrOBr_2.XH_2O$. Alternatively, one can prepare acidic solutions from the metals themselves or their oxides. For example, Sb metal can be reacted with concentrated nitric acid to obtain the hydrous oxide, which can then be dissolved in concentrated hydrochloric acid. The precipitate is washed with water, then impregnated or mixed with an oxide of molybdenum and/or vanadium, or with precursors of said oxides. A binder or support material, such as silica, can also be added to make the catalyst sufficiently attrition resistant for use in a fluidized bed reactor. The amount of binder or support so added can be, for example, in the range of about 25 to about 95 weight percent, preferably about 25 to about 60 weight percent, based on the weight of the final catalyst, including said binder or support. The resultant mixture is dried in an oven, or is spray dried, to obtain a dried composite ready for calcination.

The amounts of oxides or oxide precursors used in the preparation of the catalyst herein are critical. Thus the composition of the intimate mixture must be such that the atomic ratio of antimony to uranium is at least about 1.35:1, preferably at least about 1.50:1, but no higher than about 2.75:1, preferably no higher than about 2.5:1, the atomic ratio of the Group IV B element to uranium is at least about 0.25:1, preferably at least about 0.5:1, but no higher than about 1.65:1, preferably no higher than about 1.5:1. Especially critical is the atomic ratio of molybdenum and/or vanadium to uranium, which must be at least about 0.05:1, preferably at least about 0.08:1, but no higher than about 0.2:1, preferably no higher than about 0.15:1. In addition the atomic ratios of the sum of the antimony and the Group IV B element to uranium must be within a range of about 3.5:1 to about 2.5:1, preferably about 3.3:1 to about 2.8:1, with the most preferred ratio being about 3:1.

Once an intimate mixture of the oxides or their precursors has been prepared, it must be heated (calcined) to a critical temperature of at least about 850° C., preferably at least about 875° C., preferably in an atmosphere containing molecular oxygen, in order to obtain the defined novel catalyst. Although the temperature can be as high as about 1050° C., or even higher, in general a temperature of about 1000° C. need not be exceeded. Once having selected a critical temperature within the above range, the mixture is maintained at such temperature for a time sufficient to obtain the new catalyst herein. At the lower temperatures, longer calcination periods are required, while at the higher temperatures shorter periods will suffice. Thus, the time required for calcination can be as low as about 15 minutes, generally at least about one hour, but a period of no more than about 24 hours, generally no more than about 18 hours, is required. The heating is carried out at atmospheric pressure, although elevated pressures can be used if desired.

The catalyst obtained herein can be employed as an oxidation catalyst using conventional procedures. Thus, in the conversion of propylene to acrylonitrile, in the presence of ammonia and a gas containing molecular oxygen, such as air or oxygen itself, a gaseous mixture containing such reactants is brought into contact with the novel catalyst defined herein at a pressure of about 0 about 100 pounds per square inch gauge (about 0 to about 7.0 kilograms per square centimeter), perferably about 0 to about 50 pounds per square inch gauge (about 0 to about 3.5 kilograms per square centimeter), in a temperature range of about 375° to about 525° C., preferably about 450° to about 495° C., at a contact time of at least about 0.01 second, preferably in the range of about 0.1 to about 15 seconds. The molar ratio of oxygen to propylene is about 0.5:1 to about 5:1, perferably about 1:1 to about 2:1, while the molar ratio of ammonia to propylene is greater than about 0.5:1, but preferably no greater than about 1.5:1. By contact time we mean the bulk volume of the catalyst in cubic centimeters divided by the flow rate of the total reactants in vapor form at reaction conditions in cubic centimeters per second. The novel catalyst herein can be used in a fixed-bed or a fluidized-bed reactor.

DESCRIPTION OF PREFERRED EMBODIMENTS

The following will provide a further understanding of the invention claimed herein.

Example I $SbCl_3$ (171 grams), $UO_2(NO_3)_2.6H_2O$ (188 grams), and concentrated hydrochloric acid (1500 ml) were added to 1500 ml of water to form a clear solution. A solution of 150.8 grams of $TiOSO_4.H_2SO_4.8H_2O$ in 1500 ml of water was prepared and added to the first solution. Concentrated ammonium hydroxide (4500 ml) was added to form a precipitate. The precipitate was recovered by filtration. The filter cake was washed with 37.5 liters of water, then mixed with 824 grams of Ludox AS, an ammonia-stabilized silica sol containing 30 percent by weight $SiO_2$ made and sold by DuPont, Wilmington, Del. The resultant slurry was heated to evaporate the excess water while stirring to ensure a homogeneous mixture. After the excess water was removed, the catalyst was dried overnight in a 120° C. oven. The oven-dried material was calcined in a muffle furnace for 16 hours at 910° C.

Example II $SbCl_3$ (85.5 grams), concentrated hydrochloric acid (450 ml), and $UO_2(NO_3)_2.6H_2O$ (91.9 grams) were dissolved in 1875 ml of water. A solution of 75.4 grams of $TiOSO_4.H_2SO_4.8H_2O$ in 1875 ml of what was added to the first solution. The pH was adjusted to 8.5 with concentrated ammonium hydroxide. A precipitate formed which was recovered by filtration. The filter cake was washed with 18 liters of water, then dried at 120° C. overnight. The oven-dried material was ground to a fine powder. A 125.3-gram portion of this powder was impregnated with 0.9 gram of $(NH_4)_6MO_7O_{24}.4H_2O$ in 93.9 ml of water. The impregnated material was dried at 120° C. overnight. A 45-gram portion of the impregnated powder was added to 150 grams of Ludox AS. The resultant slurry was ball-milled for 1.5 hours. The slurry was heated to evaporate excess water, then dried overnight in a 120° C. oven. The catalyst was calcined at 930° C. for two hours to complete the preparation. The catalyst so prepared contained 50 weight percent $USb_{2.05}Ti_{1.03}Mo_{0.025}O_{9-10}$ and 50 weight percent $SiO_2$.

Examples III to VIII

Additional molybdenum-promoted catalysts were made by the procedure used in Example II except that the amounts of $SbCl_3$, $UO_2(NO_3)_2.6H_2O$, and $(NH_4)_6MO_7O_{24}.4H_2O$ employed were varied in accordance with the atomic ratios shown below in Table I. In each case the $SiO_2$ present amounted to 50 weight percent of the final catalyst.

Examples IX and X $SbCl_3$ (43 grams), concentrated hydrochloric acid (225 ml), and $UO_2(NO_3)_2.6H_2O$ (50 grams) were dissolved in 950 ml of water. To this solution were added 40 grams of $TiOSO_4.H_2SO_48H_2SO_4$ dissolved in 950 ml of water and 25 ml of concentrated sulfuric acid. The pH was adjusted to 8.5 with ammonium hydroxide solution (50% concentrated + 50% water). A precipitate formed which was recovered by filtration. The filter cake was washed with 16 liters of water, then dried overnight at 120° C. The oven-dried material was ground to a fine powder. A 60.33-gram portion of the powder was impregnated with 1.59 grams of $(NH_4)_6MO_7O_{24}.4H_2O$ in 60 ml of water and dried overnight in a 120° C. oven. The dried material was ground to a fine powder and divided into two 33.3-gram portions. One portion (Example IX) was set aside, while the other (Example X) was calcined at 500° C. for one hour. Each portion was then mixed with 101.1 grams Ludox AS and ball-milled for one hour. The samples were heated to evaporate excess water, dried at 120° C. overnight, and then calcined at 930° C. for two hours to complete the preparation. In each case the catalyst so prepared contained 50 weight percent $USb_{1.9}TiMo_{0.10}O_{9-10}$ and 50 weight percent $SiO_2$.

Examples XI and XII $SbCl_3$ (86 grams) and concentrated hydrochloric acid (450 ml) were dissolved in 1875 ml of water. To this solution were added 100 grams of $UO_2(NO_3)_2.6H_2O$ dissolved in 100 ml of water and 80 grams of $TiOSO_4.H_2SO_4.8H_2O$ dissolved in 1875 ml of water. A precipitate was formed by adjusting the pH to 8.5 with ammonium hydroxide solution. The precipitate was recovered by filtration, washed with 14 liters of water, and dried overnight at 120° C. The over-dried material was ground to a fine powder. A portion of the powder (62.5 grams) was impregnated with 61.3 ml of vanadyl oxalate solution containing 0.448 gram of vanadium. The impregnated material was dried overnight at 120° C. and divided into two 30.8-gram portions. One portion (Example XI) was set aside, while the other (Example XII) was calcined at 500° C. for one hour. Each sample was then ball-milled with 102.6 grams of Ludox AS for one hour. The resultant slurry was evaporated to dryness, dried at 120° C. overnight, and calcined at 930° C. for two hours to complete the preparation. In each case the catalyst so prepared contained 50 weight percent $USb_{1.9}TiV_{0.10}O_{9-10}$ and 50 weight percent $SiO_2$.

Example XIII $SbCl_3$ (136 grams) and concentrated hydrochloric acid (675 ml) were added to 2.0 liters of water to form a clear solution. To this solution were added 150 grams of $UO_2(NO_3)_2.6H_2O$ dissolved in 200 ml of water and 120 grams of $TiOSO_4.H_2SO_4.8H_2O$ dissolved in two liters of water. The pH of the solution was adjusted to 8.5 by adding ammonium hydroxide solution. A precipitate formed which was recovered by filtration. The filter cake was washed with 20 liters of water, then dried at 120° C. overnight. The oven-dried material was ground to a powder. A 13.3-gram portion of this powder was impregnated with an aqueous solution containing 0.047 gram of V as $VO(C_2O_4)_2$ and 0.18 gram of $(NH_4)_6Mo_7O_{24}.4H_2O$. The impregnated material was dried overnight at 120° C., then ball-milled with 44.5 grams of Ludox AS. The resultant slurry was heated to evaporate excess water, dried overnight at 120°, then calcined at 930° C. for two hours to complete the preparation. The catalyst so prepared contained 50 weight percent $USb_2TiMo_{0.05}V_{0.05}O_{9-10}$ and 50 weight percent $SiO_2$.

Each of the above catalysts was used to prepare acrylonitrile as follows. Mixtures of 20–40 mesh catalyst and 20–40 mesh quartz were changed to a 5.0 ml fixed-bed microreactor constructed from ⅜ inch (0.80 cm I.D.) stainless steel tubing. The microreactor was heated in a split-block electric furnace. Propylene, air, and ammonia in 1.0/11/1.1 molar ratio were passed over the catalyst bed. The temperature profile of the catalyst bed was determined by sliding a thermocouple along a 0.32 cm O.D. axial thermowell. The reaction temperature reported herein is the hot-spot temperature. The pressure was maintained at 0.4 pounds per square inch gauge (0.03 kilograms per square centimeter). The contact time was so adjusted so as to obtain at least 92 percent propylene conversion. Reaction was continued for a period of six hours or until there was a significant reduction in acrylonitrile yield. The reactor effluent was diluted ten to one with nitrogen or helium and analyzed by gas chromotography. The catalyst screening runs lasted six to eight hours. The results obtained are tabulated below in Table I.

Catalyst performance was characterized in terms of contact time, conversion, selectivities and yields. These are defined below:

$$\text{contact time} = \frac{\text{volume of catalyst}}{\text{total flow rate of feed gases at reaction conditions}}$$

$$\text{conversion} = \frac{\text{moles of propylene converted}}{\text{moles of propylene fed}}$$

$$\text{selectivity} = \frac{\text{moles} \times \text{carbon number}}{\text{moles of propylene converted} \times 3}$$

$$\text{yield} = \frac{\text{moles} \times \text{carbon number}}{\text{moles of propylene fed} \times 3}$$

TABLE I

| Run No. | Catalyst Example | Atomic Ratio | | | | | Contact Time, Seconds | Temp. °C. | Per Cent $C_3H_6$ Conversion | Per Cent Selectivities | | | | Length of Run, Hours |
|---|---|---|---|---|---|---|---|---|---|---|---|---|---|---|
| | | U | Sb | Ti | Mo | V | | | | $CO + CO_2$ | HCN | Aceto-nitrile | Acrylo-nitrile | |
| 1 | I | 1.0 | 2.0 | 1.0 | — | — | 1.7 | 475 | 98.2 | 12.0 | 0.4 | 1.6 | 86.0 | 0.5 |
| 2 | II | 1.0 | 2.05 | 1.03 | 0.025 | — | 1.7 | 475 | 97.8 | 10.9 | 6.1 | 2.0 | 81.2 | 0.75 |
| 3 | III | 1.0 | 2.11 | 1.05 | 0.05 | — | 1.7 | 475 | 98.7 | 11.1 | 6.8 | 1.6 | 81.0 | 1.5 |
| 4 | IV | 1.0 | 2.22 | 1.11 | 0.11 | — | 1.7 | 475 | 95.5 | 7.3 | 4.4 | 2.1 | 85.1 | 6 |
| 5 | V | 1.0 | 2.35 | 1.18 | 0.18 | — | 3.2 | 475 | 92.0 | 6.6 | 6.7 | 2.5 | 83.1 | 6 |
| 6 | VI | 1.0 | 2.5 | 1.25 | 0.25 | — | 6.5 | 475 | 96.3 | 7.9 | 6.4 | 1.5 | 83.7 | 6 |
| 7 | VII | 1.0 | 1.9 | 1.0 | .10 | — | 1.7 | 475 | 98.1 | 7.9 | 6.8 | 1.7 | 83.5 | 6 |
| 8 | VIII | 1.0 | 2.0 | 1.0 | .10 | — | 1.7 | 475 | 93.4 | 9.4 | 5.0 | 1.5 | 82.4 | 6 |
| 9 | IX | 1.0 | 1.9 | 1.0 | .10 | — | 1.1 | 475 | 100.0 | 10.3 | 7.3 | 1.3 | 80.9 | 6 |
| 10 | X | 1.0 | 1.9 | 1.0 | .10 | — | 1.7 | 472 | 97.6 | 9.1 | 7.3 | 2.3 | 80.6 | 6 |
| 11 | XI | 1.0 | 1.9 | 1.0 | — | .10 | 1.1 | 476 | 100.0 | 13.6 | 8.5 | 1.3 | 76.3 | 6 |
| 12 | XII | 1.0 | 1.9 | 1.0 | — | .10 | 1.1 | 476 | 100.0 | 10.4 | 7.4 | 1.3 | 80.9 | 6 |
| 13 | XIII | 1.0 | 2.0 | 1.0 | .05 | .05 | 1.1 | 475 | 99.4 | 7.8 | 7.2 | 1.7 | 82.5 | 6 |

Referring to Table I above, Run No. 1, using a catalyst containing solely uranium, antimony and titanium, was terminated at the end of one-half hour because of significant drop in acrylonitrile yield thereafter. The presence of molybdenum in the catalyst in Run No. 2 in an amount below the critical amount required herein did not signicantly improve the length of reaction time sufficient to maintain high acrylonitrile yield. However, in Run No. 3 the presence of additional molybdenum within the critical ranges required herein significantly increased reaction time to 1.5 hours. In each of Runs 3 to 13 wherein increased amounts of molybdenum, vanadium or both were present, there was no appreciable reduction in acrylonitrile yield at the end of six hours.

Several of the catalysts that performed well in the above screening runs, namely catalysts prepared in Examples V, VII, X and XI, were further tested in reactions converting propylene, ammonia and molecular oxygen to acrylonitrile. Five grams of 20–40 mesh catalyst were charged to a U-shaped reactor tube constructed from ¼ inch (0.48 cm I.D.) stainless steel tubing. The charged reactor was immersed in a fluidized sand bath for heating. The feed gases were metered through electronic mass flow controllers, to ensure a constant flow of reactants when the unit was unattended. The reaction temperature was monitored by a sheathed thermocouple inserted into the catalyst bed. The reactor effluent stream was diluted then to one with nitrogen or helium and analyzed several times a day by gas chromatography. The reaction was continued until yield of acrylonitrile fell to about 70 percent. The catalyst was then regenerated by turning off the propylene and ammonia flows and allowing air to continue. Acrylonitrile product was then resumed as before and the product was analyzed at the end of one hour. The data are summarized below in Tables II, III, IV and V. The catalyst of Example V was used in Table II, of Example VII in Table III, of Example X in Table IV and of Example XI in Table V. In each case the molar ratio of propylene, air and ammonia was 1.0:11:1.1. The reaction temperature in Tables II, III and IV was 475° C. and in Table V 450° C. In Tables II and IV the pressure was 2.7 pounds per square inch gauge (0.2 kg/cm²) and in Tables III and IV 2.1 pounds per square inch gauge (0.15 kg/cm²).

The contact time in Table II was 2.9 seconds, in Table III 1.9 seconds, in Table IV 1.7 seconds and in Table V 1.8 seconds. In each of Tables II, III and IV regeneration of catalyst was carried out for 16 hours and in Table V for 64 hours.

TABLE II

| | Per Cent | Acrylonitrile | Per Cent Selectivities | | | |
|---|---|---|---|---|---|---|
| Hours | $C_3H_6$ Converted | Yield Mole Per Cent | $CO + CO_2$ | HCN | Aceto-nitrile | Acrylo-nitrile |
| 1 | 97.5 | 75.4 | 9.5 | 11.0 | 2.1 | 77.3 |
| 24 | 96.7 | 79.7 | 5.6 | 9.5 | 1.8 | 82.4 |
| 120 | 96.8 | 81.9 | 4.3 | 8.4 | 1.8 | 84.6 |
| 169 | 96.9 | 80.3 | 6.4 | 8.0 | 1.9 | 82.9 |
| 192 | 96.1 | 70.5 | 13.3 | 10.2 | 2.2 | 73.4 |
| After Regeneration | | | | | | |
| 1 | 98.0 | 86.2 | 4.5 | 5.5 | 2.0 | 87.8 |

TABLE III

| | Per Cent | Acrylonitrile | Per Cent Selectivities | | | |
|---|---|---|---|---|---|---|
| Hours | $C_3H_6$ Converted | Yield Mole Per Cent | $CO + CO_2$ | HCN | Aceto-nitrile | Acrylo-nitrile |
| 1 | 98.8 | 79.9 | 9.7 | 8.3 | 1.1 | 80.9 |
| 24 | 98.8 | 81.0 | 8.9 | 7.9 | 1.0 | 82.0 |
| 408 | 98.8 | 80.8 | 9.4 | 7.9 | 1.0 | 81.8 |
| 432 | 98.6 | 70.8 | 17.0 | 9.9 | 1.0 | 71.8 |
| 459 | 98.6 | 67.9 | 18.6 | 11.6 | 1.0 | 68.9 |
| After Regeneration | | | | | | |
| 1 | 98.7 | 82.7 | 8.3 | 6.8 | 1.0 | 83.8 |

TABLE IV

| | Per Cent | Acrylonitrile | Per Cent Selectivities | | | |
|---|---|---|---|---|---|---|
| Hours | $C_3H_6$ Converted | Yield Mole Per Cent | $CO + CO_2$ | HCN | Aceto-nitrile | Acrylo-nitrile |
| 2 | 99.6 | 83.0 | 7.7 | 7.1 | 1.7 | 83.3 |
| 22 | 99.6 | 81.2 | 9.1 | 7.5 | 1.7 | 81.5 |
| 166 | 99.6 | 81.0 | 9.2 | 7.6 | 1.7 | 81.3 |
| 190 | 99.6 | 80.5 | 9.8 | 8.1 | 1.3 | 80.8 |
| 214 | 99.7 | 77.1 | 11.3 | 10.0 | 1.3 | 77.3 |
| 238 | 99.7 | 75.3 | 14.1 | 9.0 | 1.3 | 75.5 |
| 262 | 99.8 | 72.5 | 16.0 | 9.8 | 1.3 | 72.7 |
| 269 | 99.7 | 72.4 | 16.3 | 9.2 | 1.5 | 72.7 |
| After Regeneration | | | | | | |
| 1 | 99.9 | 84.5 | 6.5 | 7.5 | 1.3 | 84.6 |

TABLE V

| | Per Cent | Acrylonitrile | Per Cent Selectivities | | | |
|---|---|---|---|---|---|---|
| Hours | $C_3H_6$ Converted | Yield Mol Per Cent | $CO + CO_2$ | HCN | Aceto-nitrile | Acrylo-nitrile |
| 1 | 100.0 | 76.1 | 12.6 | 9.7 | 1.6 | 76.1 |
| 24 | 100.0 | 80.3 | 9.3 | 8.9 | 1.5 | 80.3 |
| 72 | 100.0 | 79.8 | 9.7 | 8.8 | 1.6 | 79.8 |
| 240 | 100.0 | 80.0 | 9.5 | 8.9 | 1.6 | 80.0 |
| 331 | 99.6 | 78.8 | 11.3 | 8.2 | 1.6 | 78.8 |
| 355 | 99.6 | 76.7 | 12.7 | 8.5 | 1.8 | 77.0 |
| 379 | 99.6 | 75.2 | 13.4 | 8.9 | 1.8 | 75.5 |
| 383 | 99.7 | 74.5 | 14.6 | 8.9 | 1.8 | 74.7 |
| 407 | 99.7 | 72.1 | 16.4 | 9.3 | 1.8 | 72.3 |
| 414 | 99.3 | 70.6 | 17.6 | 9.4 | 1.9 | 71.1 |
| After Regeneration | | | | | | |
| 1 | 99.8 | 81.1 | 10.1 | 7.0 | 1.6 | 81.3 |

The data in Tables II, III, IV and V are quite striking. While in Runs Nos. 1 and 2, wherein catalysts falling outside the claimed range were used in preparing acrylonitrile, reduction in acrylonitrile yield occurred in less than 0.75 hour, catalyst life was extended to at least 192 hours (Table II) and as long as 459 hours (Table III) when critical amounts of molybdenum and/or vanadium were present. In addition acrylonitrile yields and selectivities using the regenerated catalyst were higher than with the fresh catalyst.

Although the novel catalyst herein has been shown to be very effective in the ammoxidation of propylene to acrylonitrile, the catalyst can also be used advantageously in other ammoxidation reactions such as the ammoxidation of isobutylene to methacrylonitrile, and in oxidation reactions, such as oxidation reactions converting propylene to acrolein, isobutylene to methacrolein, butene-1 or butene-2 to 1,3-butadiene, and isoamylenes to isoprene.

Obviously, many modifications and variations of the invention, as hereinabove set forth, can be made without departing from the spirit and scope thereof, and, therefore, only such limitations should be imposed as are indicated in the appended claims.

We claim:

1. The novel catalyst wherein the atomic ratios of the components thereof are defined by the following empirical formula:

$$USb_aX_bY_cO_d,$$

wherein X is an element from Group IV B of the Periodic Table; Y is at least one element selected from the group consisting of molybdenum and vanadium; a is a number falling within the range of about 1.35 to about 2.75; b is a number falling within the range of about 0.25 to about 1.65; c is a number falling within the range of about 0.05 to about 0.2, d is a number falling within the range of about 8 to about 12; and the sum of a+b is a number falling within the range of about 2.5 to about 3.5.

2. The catalyst of claim 1 wherein the Group IV B element is titanium.

3. The catalyst of claim 1 wherein the Group IV B element is zirconium.

4. The catalyst of claim 1 wherein the Group IV B element is hafnium.

5. The catalyst of claim 1 wherein Y is the element of molybdenum.

6. The catalyst of claim 1 wherein Y is the element vanadium.

7. The catalyst of claim 1 wherein Y includes molybdenum and vanadium.

8. The catalyst of claim 1 wherein the a is a number falling within the range of about 1.50 to about 2.50; b is a number falling within the range of about 0.50 to about 1.50; c is a number falling within the range of about 0.08 to about 0.15; d is a number falling within the range of about 9 to about 11; and the sum of a+b is a number falling within the range of about 2.8 to about 3.3.

9. The catalyst of claim 1 whereing the Group IV B element is titanium; a is a number falling within the range of about 1.5 to about 2.50; b is a number falling within the range of about 0.5 to about 1.50; c is a number within the range of about 0.08 to about 0.15; d is a number falling within the range of about 9 to about 11; and the sum of a+b is a number falling within the range of about 2.8 to about 3.3.

* * * * *